United States Patent [19]

Cassidy et al.

[11] Patent Number: 4,831,050
[45] Date of Patent: May 16, 1989

[54] PYRROLIDINYL BENZOPYRANS AS HYPOTENSIVE AGENTS

[75] Inventors: Frederick Cassidy; Erol A. Faruk, both of Harlow, England

[73] Assignee: Beecham Group p.l.c., England

[21] Appl. No.: 111,770

[22] Filed: Oct. 21, 1987

[51] Int. Cl.[4] .................. C07D 405/00; A61K 31/40; C07F 493/00
[52] U.S. Cl. ..................... 514/422; 548/525; 548/407
[58] Field of Search ................ 548/525, 407; 514/422, 548/407; 514/409

[56] References Cited

U.S. PATENT DOCUMENTS

| | | | |
|---|---|---|---|
| 4,446,113 | 12/1985 | Evans et al. | 548/525 |
| 4,510,152 | 4/1985 | Faruk | 548/525 |
| 4,542,149 | 9/1985 | Evans et al. | 548/525 |
| 4,555,509 | 11/1985 | Evans et al. | 548/525 |
| 4,610,992 | 9/1986 | Evans et al. | 548/525 |
| 4,640,928 | 2/1987 | Willcocks | 548/525 |
| 4,644,070 | 2/1987 | Evans et al. | 548/525 |
| 4,647,670 | 3/1987 | Evans et al. | 548/525 |

FOREIGN PATENT DOCUMENTS 1548221 7/1979 United Kingdom ................ 548/525

Primary Examiner—Mary C. Lee
Assistant Examiner—Robert C. Whittenbaugh
Attorney, Agent, or Firm—Jacobs & Jacobs

[57] ABSTRACT

Compounds of formula (I):

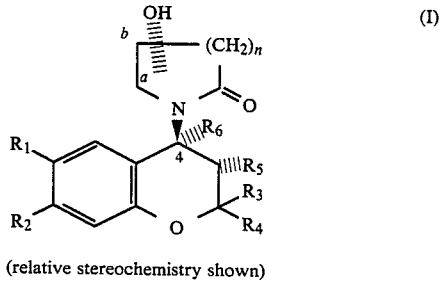

(relative stereochemistry shown)

wherein:
either one of $R_1$ and $R_2$ is hydrogen and the other is selected from the class of $C_{1-6}$ alkylcarbonyl, $C_{1-6}$ alkoxycarbonyl, $C_{1-6}$ alkylcarbonyloxy, $C_{1-6}$ alkyl-hydroxymethyl, nitro, cyano, chloro, trifluoromethyl, $C_{1-6}$ alkylsulphinyl, $C_{1-6}$ alkylsulphonyl, $C_{1-6}$ alkoxysulphinyl, $C_{1-6}$ alkoxysulphonyl, $C_{1-6}$ alkylcarbonylamino, $C_{1-6}$ alkoxycarbonylamino, $C_{1-6}$ alkyl-thiocarbonyl, $C_{1-6}$ alkoxy-thiocarbonyl, $C_{1-6}$ alkyl-thiocarbonyloxy, 1-mercapto $C_{2-7}$ alkyl, formyl, or aminosulphinyl, aminosulphonyl or aminocarbonyl, the amino moiety being optionally substituted by one or two $C_{1-6}$ alkyl groups, or $C_{1-6}$ alkylsulphinylamino, $C_{1-6}$ alkylsulphonylamino, $C_{1-6}$ alkoxysulphinylamino or $C_{1-6}$ alkoxysulphonylamino, or ethylenyl terminally substituted by $C_{1-6}$ alkylcarbonyl, nitro or cyano, or —C($C_{1-6}$ alkyl(NOH or —C($C_{1-6}$ alkyl)NNH$_2$, or one of $R_1$ and $R_2$ is nitro, cyano or $C_{1-3}$ alkylcarbonyl and the other is methoxy or amino optionally substituted by one or two $C_{1-6}$ alkyl or by $C_{2-7}$ alkanoyl;
one of $R_3$ and $R_4$ is hydrogen or $C_{1-4}$ alkyl and the other is $C_{1-4}$ alkyl or $R_3$ and $R_4$ together are $C_{2-5}$ polymethylene;
either $R_5$ is hydrogen, hydroxy, $C_{1-6}$ alkoxy or $C_{1-7}$ acyloxy and $R_6$ is hydrogen or $R_5$ and $R_6$ together are a bond; and
n is 1 or 2;
the hydroxy group substituting the lactam group is other than at position a; and the substituted lactam group being trans to the $R_5$ group when $R_5$ is hydroxy, $C_{1-6}$ alkoxy or $C_{1-7}$ acyloxy; or a pharmaceutically acceptable salt thereof; having antihypertensive activity, a process for their preparation and their use as pharmaceuticals.

9 Claims, No Drawings

PYRROLIDINYL BENZOPYRANS AS HYPOTENSIVE AGENTS

The present invention relates to novel chromans and chromenes having pharmacological activity, to a process for preparing them, to pharmaceutical compositions containing them, and to their use in the treatment of mammals.

European Patent Publication Nos. 76 075, 91 748 and, 93 535 disclose classes of chromans and chromenes that are described as having blood pressure lowering activity.

A further class of chromans and chromenes has now been discovered which contain a lactam ring that substitutes the chroman or chromene in the 4-position, the lactam ring having an hydroxy substituent. In addition, such chromans and chromenes have been found to have blood pressure lowering activity. It is also believed that these compounds have a mechanism of action which indicates that they are of potential use in the treatment of other cardiovascular disorders such as congestive heart failure, angina, peripheral vascular disease and cerebral vascular disease; and disorders associated with smooth muscle contraction of the gastro-intestinal tract (such as irritable bowel syndrome and diverticular disease), respiratory system (such as reversible airways obstruction and asthma), uterus (such as premature labour) and urinary tract (such as incontinence).

Accordingly, the present invention provides a compound of formula (I):

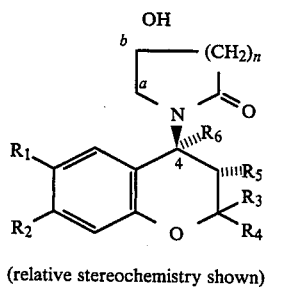

(relative stereochemistry shown)

wherein:
either one of $R_1$ and $R_2$ is hydrogen and the other is selected from the class of $C_{1-6}$ alkylcarbonyl, $C_{1-6}$ alkoxycarbonyl, $C_{1-6}$ alkylcarbonyloxy, $C_{1-6}$ alkylhydroxymethyl, nitro, cyano, chloro, trifluoromethyl, $C_{1-6}$ alkylsulphinyl, $C_{1-6}$ alkylsulphonyl, $C_{1-6}$ alkoxysulphinyl, $C_{1-6}$ alkoxysulphonyl, $C_{1-6}$ alkylcarbonylamino, $C_{1-6}$ alkoxycarbonylamino, $C_{1-6}$ alkyl-thiocarbonyl, $C_{1-6}$ alkoxy-thiocarbonyl, $C_{1-6}$ alkyl-thiocarbonyloxy, 1-mercapto $C_{2-7}$ alkyl, formyl, or aminosulphinyl, aminosulphonyl or aminocarbonyl, the amino moiety being optionally substituted by one or two $C_{1-6}$ alkyl groups, or $C_{1-6}$ alkylsulphinylamino, $C_{1-6}$ alkylsulphonylamino, $C_{1-6}$ alkoxysulphinylamino or $C_{1-6}$ alkoxysulphonylamino, or ethylenyl terminally substituted by $C_{1-6}$ alkylcarbonyl, nitro or cyano, or —C($C_{1-6}$ alkyl)NOH or —C($C_{1-6}$ alkyl)NNH$_2$, or one of $R_1$ and $R_2$ is nitro, cyano or $C_{1-3}$ alkylcarbonyl and the other is methoxy or amino optionally substituted by one or two $C_{1-6}$ alkyl or by $C_{2-7}$ alkanoyl;
one of $R_3$ and $R_4$ is hydrogen or $C_{1-4}$ alkyl and the other is $C_{1-4}$ alkyl or $R_3$ and $R_4$ together are $C_{2-5}$ polymethylene;
either $R_5$ is hydrogen, hydroxy, $C_{1-6}$ alkoxy or $C_{1-7}$ acyloxy and $R_6$ is hydrogen or $R_5$ and $R_6$ together are a bond; and
n is 1 or 2;
the hydroxy group substituting the lactam group is other than at position a; and the substituted lactam group being trans to the $R_5$ group when $R_5$ is hydroxy, $C_{1-6}$ alkoxy or $C_{1-7}$ acyloxy; or a pharmaceutically acceptable salt thereof.

When one of $R_1$ and $R_2$ is hydrogen, the other is preferably selected from the class of $CF_3$, $C_{1-6}$ alkylcarbonyl, $C_{1-6}$ alkoxycarbonyl, nitro or cyano. In particular, when one of $R_1$ and $R_2$ is hydrogen, the other is preferably acetyl, nitro or cyano, especially nitro or cyano.

When one of $R_1$ and $R_2$ is hydrogen, it is preferred that $R_2$ is hydrogen.

When one of $R_1$ and $R_2$ is nitro, cyano or $C_{1-3}$ alkylcarbonyl, the other is preferably amino optionally substituted by one or two $C_{1-6}$ alkyl or by $C_{2-7}$ alkanoyl. In particular, when one of $R_1$ and $R_2$ is nitro, cyano or $C_{1-3}$ alkylcarbonyl, the other is amino, methylamino, dimethylamino or acetylamino. Most preferably, one of $R_1$ and $R_2$ is nitro or cyano, especially cyano, and the other is amino.

When one of $R_1$ and $R_2$ is nitro, cyano or $C_{1-3}$ alkylcarbonyl, it is preferred that $R_1$ is nitro, cyano or $C_{1-3}$ alkylcarbonyl.

The alkyl groups or alkyl moieties of alkyl-containing groups for $R_1$ and $R_2$ are, preferably, methyl or ethyl.

Preferably, $R_3$ and $R_4$ are both $C_{1-4}$ alkyl. In particular, they are both methyl or ethyl, preferably both methyl.

When $R_5$ is $C_{1-6}$ alkoxy and $R_6$ is hydrogen, preferred examples of $R_5$ include methoxy and ethoxy, of which methoxy is more preferred. When $R_5$ is $C_{1-7}$ acyloxy and $R_6$ is hydrogen, a preferred class of $R_5$ is unsubstituted carboxylic acyloxy, such as unsubstituted aliphatic acyloxy or benzoyloxy. However, it is more preferred that $R_5$ and $R_6$ together are a bond or that $R_5$ and $R_6$ are both hydrogen, or, in particular, that $R_5$ is hydroxy and $R_6$ is hydrogen.

The hydroxy substituent on the lactam ring is preferably at position 3- or 4-relative to the lactam nitrogen atom (position 1), when n=1.

n is preferably 1.

The compounds of formula (I) are preferably in pharmaceutically acceptable form. By pharmaceutically acceptable form is meant, inter alia, of a pharmaceutically acceptable level of purity excluding normal pharmaceutical additives such as diluents and carriers, and including no material considered toxic at normal dosage levels. A pharmaceutically acceptable level of purity will generally be at least 50% excluding normal pharmaceutical additives, preferably 75%, more preferably 90% and still more preferably 95%. One preferred pharmaceutically acceptable form is the crystalline form, including such form in a pharmaceutical composition.

Examples of a pharmaceutically acceptable salt of a compound of formula (I) include the acid addition salts of a compound of formula (I), wherein one or the other of $R_1$ and $R_2$ is an amino or an amino-containing group, for example the hydrochloride and hydrobromide salts.

The compounds of formula (I) and salts thereof may form pharmaceutically acceptable solvates, such as hydrates and these are included wherever a compound of formula (I) or a salt thereof is herein referred to.

The compounds of formula (I), have at least one asymmetric centre and, therefore, can exist in more than one isomeric form. The present invention extends to all such isomers individually and as mixtures, such as racemic modifications. The isomers may be separated one from another by conventional methods, such as by chromatography. Alternatively, an optically pure isomer may be prepared using chiral intermediates.

The hydroxy group substitutes the lactam ring in the α-configuration (wherein the hydroxy group is below the plane of the lactam ring as depicted in formula (I)).

Examples of compounds of formula (I) include the compounds prepared in the Examples hereinafter.

The present invention also provides a process for the preparation of a compound of formula (I), which comprises the reaction of a compound of formula (II):

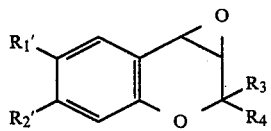

with an anion of formula (III):

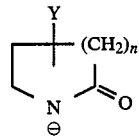

wherein Y is hydroxy, protected hydroxy or an oxo group; $R_1'$ is $R_1$ as hereinbefore defined or a group or atom convertible thereto, $R_2'$ is $R_2$ as hereinbefore defined or a group or atom convertible thereto, and $R_3$, $R_4$, $R_5$, and $R_6$ are as hereinbefore defined; and thereafter converting Y when protected hydroxy to hydroxy or reducing Y when oxo group to hydroxy;

or (when the hydroxy substituent on the lactam ring is in position b as depicted in formula (I)); with $NH_3$ to give a compound of formula (IV):

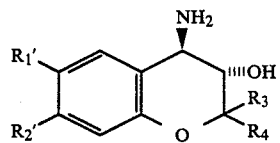

wherein the variable groups are as hereinbefore defined; and thereafter reacting the compound of formula (IV) with a compound of formula (V):

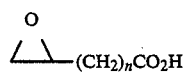

wherein n is as defined in formula (I); and thereafter in the case where $R_1'$ is a group or atom convertible into $R_1$, converting the group or atom into $R_1$; in the case where $R_2'$ is a group or atom convertible into $R_2$, converting the group or atom into $R_2$; optionally converting $R_1$ or $R_2$ in the resulting compound of formula (I) into another $R_1$ or $R_2$; optionally converting the resulting compound of formula (I), wherein $R_5$ is hydroxy and $R_6$ is hydrogen, into another compound of formula (I) wherein $R_5$ is $C_{1-6}$ alkoxy or $C_{1-7}$ acyloxy and $R_6$ is hydrogen, or optionally dehydrating the resulting compound of formula (I), wherein $R_5$ is hydroxy and $R_6$ is hydrogen, so as to obtain the corresponding compound of formula (I), wherein $R_5$ and $R_6$ together are a bond, and optionally reducing the resulting compound of formula (I), wherein $R_5$ and $R_6$ together are a bond, so as to obtain the corresponding compound of formula (I) wherein $R_5$ and $R_6$ are both hydrogen; and optionally forming a pharmaceutically acceptable salt or solvate.

The reaction is preferably carried out in an inert solvent such as dimethylformamide or dimethylsulphoxide in the presence of a base such as sodium hydride.

Deprotection of Y when protected hydroxy to hydroxy may be carried out by conventional methods, such as hydrolysis.

Reduction of a Y oxo group to hydroxy may be carried out by conventional hydride reducing agents such as sodium borohydride in an inert solvent such as dimethylsulphoxide.

Examples of conversions of a group or atom for $R_1'$ or $R_2'$ into $R_1$ or $R_2$ are generally known in the art of aromatic chemistry. For example, if it is desired to obtain a compound of formula (I), wherein one of $R_1$ and $R_2$ is hydrogen and the other is nitro, it is possible to carry out the reaction between the compounds of formulae (II) and (III) with one of $R_1'$ and $R_2'$ being hydrogen and the other being acetamido and then to nitrate the resulting compound in conventional manner and subsequently to convert the acetamido group into a hydrogen atom by hydrolysis, diazotisation and decomposition in conventional manner.

If the optional conversion of the resulting compound of formula (I) wherein $R_5$ is hydroxy and $R_6$ is hydrogen, into another compound of formula (I) wherein $R_5$ is $C_{1-7}$ acyloxy and $R_6$ is hydrogen, is to be carried out, then it is preferred first to protect any unsubstituted terminal amine that may be present for $R_1$ or $R_2$ and after the acylation reaction to convert the protected amino moiety into the required terminal amine. Examples of protecting group and their addition and removal are generally known in the art. Similarly, the hydroxy substituent on the lactam moiety is preferably protected; or Y is an oxo group which is then converted to hydroxy by reduction as hereinbefore described.

Examples of an optional conversion of $R_1$ or $R_2$ in the resulting compound of formula (I) into another $R_1$ or $R_2$, as hereinbefore defined, include the optional conversion of an α-hydroxyethyl group into acetyl by oxidation, the optional conversion of an amino group into a chloro atom by diazotisation and reaction with a chloride salt, the optional conversion of an amino group into an amino group substituted by one or two $C_{1-6}$ alkyl or by $C_{2-7}$ alkanoyl, or the optional conversion of a hydrogen atom into a nitro group by nitration.

The optional conversion of the resulting compound of formula (I) wherein $R_5$ is hydroxy and $R_6$ is hydrogen, into another compound of formula (I) wherein $R_5$ is $C_{1-6}$ alkoxy or $C_{1-7}$ acyloxy and $R_6$ is hydrogen, may be carried out respectively by alkylation using an alkyl iodide in an inert solvent, such as toluene, in the presence of a base, such as potassium hydroxide, or by acylation using a carboxylic acid chloride or anhydride in a non-hydroxylic solvent in the presence of a base such as trimethylamine, triethylamine or piperidine.

The optional dehydration of the resulting compound of formula (I) wherein $R_5$ is hydroxy and $R_6$ is hydrogen, so as to obtain the corresponding compound of formula (I) wherein $R_5$ and $R_6$ together are a bond, may be carried out under conventional dehydration conditions, for example, by using a dehydrating agent, such as sodium hydride, in an inert solvent, such as dry tetrahydrofuran, at reflux temperature Again, the hydroxy substituent on the lactam moiety is preferably protected for such conversions.

The optional reduction of the resulting compound of formula (I) wherein $R_5$ and $R_6$ together are a bond, so as to obtain the corresponding compound of formula (I) wherein $R_5$ and $R_6$ are both hydrogen, may be carried out in conventional manner by catalytic hydrogenation using palladium on charcoal.

The optional formation of a pharmaceutically acceptable salt, when one or the other of $R_1$ and $R_2$ in the resulting compound of formula (I) is amino or an amino-containing group, may be carried out conventionally.

It will be appreciated that the above process results in a mixture of $\alpha$- and $\beta$-hydroxy isomers in the lactam ring, which isomers may be separated to give the required $\alpha$-isomer, by conventional methods, such as by chromatography.

The compounds of formula (II) are known compounds and can be prepared in accordance with the processes described in the aforementioned U.S. patents and European Patent Publications.

Compounds of the formula (III) are known or are prepared conventionally.

It is preferred that the compounds of formula (I) are isolated in substantially pure form.

As mentioned previously, the compounds of formula (I) have been found to have blood-pressure lowering activity. They are therefore useful in the treatment of hypertension. They are also of potential use in the treatment of other disorders hereinbefore referred to.

The present invention accordingly provides a pharmaceutical composition which comprises a compound of formula (I) or a pharmaceutically acceptable salt thereof and a pharmaceutically acceptable carrier. In particular, the present invention provides an anti-hypertensive pharmaceutical composition which comprises an anti-hypertensive effective amount of a compound of formula (I) or a pharmaceutically acceptable salt thereof and a pharmaceutically acceptable carrier.

The compositions are preferably adapted for oral administration. However, they may be adapted for other modes of administration, for example parenteral administration for patients suffering from heart failure. Other alternative modes of administration include sub-lingual or transdermal administration, or inhalation, for the treatment of respiratory disorders.

In order to obtain consistency of administration it is preferred that a composition of the invention is in the form of a unit-dose. Suitable unit dose forms include tablets, capsules and powders in sachets or vials. Such unit dose forms may contain from 1 to 100 mg of a compound of the invention and more usually from 2 to 50 mg, for example 5 to 25 mg such as 6, 10 15 or 20 mg. Such compositions may be administered from 1 to 6 times a day, more usually from 2 to 4 times a day, in a manner such that the daily dose is from 1 to 200 mg for a 70 kg human adult and more particularly from 1 to 10 mg.

With the above indicated dosage range, no adverse toxicological effects are indicated with the compounds of the invention.

The compositions of the invention may be formulated with conventional excipients, such as a filler, a disintegrating agent, a binder, a lubricant, a flavouring agent. They are formulated in conventional manner, for example in a manner similar to that used for known anti-hypertensive agents, diuretics and $\beta$-blocking agents.

It is greatly preferred that the compound of formula (I) or a pharmaceutically acceptable salt thereof is administered in the form of a unit-dose composition, such as a unit dose oral or parenteral composition.

Such compositions are prepared by admixture and are suitably adapted for oral o parenteral administration, and as such may be in the form of tablets, capsules, oral liquid preparations, powders, granules, lozenges, reconstitutable powders, injectable and infusable solutions or suspensions or suppositories. Orally administrable compositions are preferred, in particular shaped oral compositions, since they are more convenient for general use.

Tablets and capsules for oral administration are usually presented in a unit dose, and contain conventional excipients such as binding agents, fillers, diluents, tabletting agents, lubricants, disintegrants, colourants, flavourings, and wetting agents. The tablets may be coated according to well known methods in the art.

Suitable fillers for use include cellulose, mannitol, lactose an other similar agents. Suitable disintegrants include starch, polyvinylpyrrolidone and starch derivatives such as sodium starch glycollate. Suitable lubricants include, for example, magnesium stearate. Suitable pharmaceutically acceptable wetting agents include sodium lauryl sulphate.

These solid oral compositions may be prepared by conventional methods of blending, filling, tabletting or the like. Repeated blending operations may be used to distribute the active agent throughout those compositions employing large quantities of fillers. Such operations are, of course, conventional in the art.

Oral liquid preparations may be in the form of, for example, aqueous or oily suspensions, solutions, emulsions, syrups, or elixirs, or may be presented as a dry product for reconstitution with water or other suitable vehicle before use. Such liquid preparations may contain conventional additives such as suspending agents, for example sorbitol, syrup, methyl cellulose, gelatin, hydroxyethylcellulose, carboxymethyl cellulose, aluminium stearate gel or hydrogenated edible fats, emulsifying agents, for example lecithin, sorbitan monooleate, or acacia; non-aqueous vehicles (which may include edible oils), for example almond oil, fractionated coconut oil, oily esters such as esters of glycerine, propylene glycol, or ethyl alcohol; preservatives, for example methyl or propyl p-hydroxybenzoate or sorbic acid, and if desired conventional flavouring or colouring agents.

Oral formulations also include conventional sustained release formulations, such as tablets or granules having an enteric coating.

For parenteral administration, fluid unit dose forms are prepared containing a compound of the present invention and a sterile vehicle. The compound, depending on the vehicle and the concentration, can be either suspended or dissolved. Parenteral solutions are normally prepared by dissolving the compound in a vehicle and filter sterilising before filling into a suitable vial or ampoule and sealing. Advantageously, adjuvants such as a local anaesthetic, preservatives and buffering agents are also dissolved in the vehicle. To enhance the stability, the composition can be frozen after filling into the vial and the water removed under vacuum.

Parenteral suspensions are prepared in substantially the same manner except that the compound is suspended in the vehicle instead of being dissolved and sterilised by exposure to ethylene oxide before suspending in the sterile vehicle. Advantageously, a surfactant or wetting agent is included in the composition to facilitate uniform distribution of the compound of the invention.

In addition such compositions may contain further active agents such as anti-hypertensive agents and diuretics.

As is common practice, the compositions will usually be accompanied by written or printed directions for use in the medical treatment concerned.

The present invention further provides a compound of the formula (I) or a pharmaceutically acceptable salt thereof for use as an active therapeutic substance, in particular in the treatment of hypertension.

The present invention yet further provides a method of treating hypertension in mammals including man, which comprises administering to the suffering mammal an anti-hypertensive effective amount of a compound of formula (I) or a pharmaceutically acceptable salt thereof or a pharmaceutical composition of the invention.

The following examples relate to the preparation of compounds of formula (I).

EXAMPLE 1

(±)-Trans-6-Cyano-3,4-dihydro-2,2-dimethyl-4-(3-hydroxy-2-oxo-1-pyrrolidinyl)-2H-1-benzopyran-3-ol

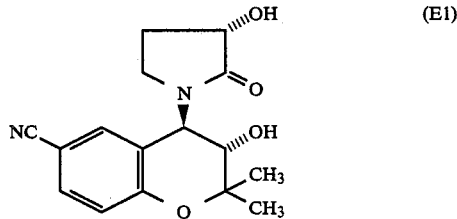

Sodium hydride (80% dispersion in oil, 1.6 g) was added to a solution of (±)-6-cyano-3,4-dihydro-2,2-dimethyl-trans-3-bromo-4-hydroxy-2H-1-benzopyran (14.86 g) in DMSO (100 mL) and the mixture stirred under a dry atmosphere for 45 min when a solution of the 3,4-epoxide resulted. The solution was then cooled to ca 10° C. before 3-trimethylsilyloxy-2-pyrrolidinone (12.86 g) was added along with further DMSO (20 mL) and sodium hydride (2.35 g). The mixture was stirred at room temperature for 22 h after which it was poured into water (600 mL) and extracted with ethyl acetate several times. The combined extracts were washed with water (4×150 mL), brine and dried (Na$_2$SO$_4$). Evaporation gave a crystalline greenish solid (14.4 g) which was triturated with a little ethyl acetate before filtering under suction and washing with a little ethyl acetate followed by 50% ether/ethyl acetate. The crystalline material (7.9 g, 50%) appeared to be a ca 50:50 mixture of the 3'-hydroxy isomers.

Separation of a small sample on a hypersil 250 mm×7 mm using a gradient elution technique with CH$_2$Cl$_2$→CH$_2$Cl$_2$— MeOH (10%) at 5 mL/min, on an LKB HPLC system at 252 nm, gave the (±)-3'β-hydroxy compound mp 282°–284° C. (from MeOH); NMR (CD$_3$OD)δ 1.27 (s, 3H), 1.51 (s, 3H), 1.97 (m, 1H), 2.45 (m, 1H), 3.06 (m, 1H), 3.42 (m, 1H), 3.89 (d, J=10, 1H), 4.53 (t, J=8,8, 1H), 5.10 (m, 1H), 6.92 (d, J=9, 1H), 7.28 (br.s, 1H), 7.52 (q, J=9,2, 1H), and the (±)-3'α-hydroxy compound (E1) mp 238°–242° C.; NMR (CD$_3$OD) δ 1.27 (s, 3H), 1.50 (s, 3H), 1.89 (m, 1H), 2.49 (m, 1H), 3.00 (m, 1H), 3.32 (m, 1H), 3.78((d, J=10, 1H), 4.47 (t, J=8, 1H), 5.13 (d, J=10, 1H), 6.93 (d, J=9, 1H), 7.40 (d, J=2, 1H), 7.53 (q, J=9,2, 1H).

EXAMPLE 2

(±)-Trans-6-Cyano-3,4-dihydro-2,2-dimethyl-4-(4-hydroxy-2-oxo-1-pyrrolidinyl)-2H-1-benzopyran-3-ol

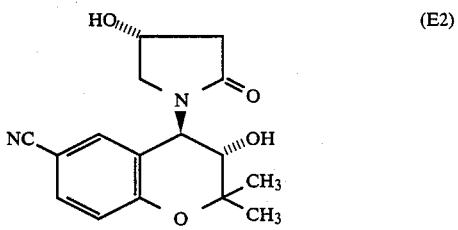

To a stirred solution of (±)-trans-6-cyano-3,4-dihydro-2,2-dimethyl-4-(2,4-dioxo-1-pyrrolidinyl)-2H-1-benzopyran -3-ol (0. g) in dry DMSO under N$_2$, was added NaBH$_4$ (0.11 g). The reaction was stirred for 3 h at room temperature. Water (100 mL) was added add the aqueous phase extracted with EtOAc. The organic layer was washed with H$_2$O add brine, dried over MgSO$_4$, filtered and evaporated to give the crude product (0.5 g) as an orange solid. This mixture was chromatographed (chromatotron CHCl$_3$→CHCl$_3$-10% MeOH gradient elution; 2 mm silica gel) to give two fractions.

Recrystallization of the least polar component (EtOAc-EtOH) gave the (±)-4'-β-hydroxy compound (0.16 g) mp 256°–259° C.; NMR [(CD$_3$)$_2$SO] δ 1.19 (s, 3H), 1.44 (s, 3H), 2.22 (q, J=18,4, 1H), 2.78 (q, J=18,6, 1H), 3.19 (m, 2H), 3.76 (m, 1H), 4.38 (m, 1H), 4.91 (m, 1H), 5.27 (d, J=4, 1H exchangeable with D$_2$O), 5.69 (d, J=6, 1H exchangeable with D$_2$O), 6.93 (d, J=8, 1H), 7.38 (narrow m, 1H), 7.60 (q, J=8,2, 1H).

In a similar recrystallisation the more polar component gave the (±)-4'-α-hydroxy compound (0.05 g) (E2) mp 259°–263° C.; NMR [(CD$_3$)$_2$SO] δ 1.21 (s, 3H), 1.46 (s, 3H), 2.24 (d, J=18, 1H), 2.70 (m, 2H), 3.50 (q, J=10,4, 1H), 3.63 (q, J=10,6, 1H), 4.31 (m, 1H), 5.00 (d, J=10, 1H), 5.26 (d, J=4, 1H exchangeable with D$_2$O), 5.73 (d, J=6, 1H exchangeable with D$_2$O), 6.94 (d, J=9, 1H), 7.38 (narrow m, 1H), 7.61 (q, J=9,2, 1H).

EXAMPLE 3

(−)-Trans-6-Cyano-3,4-dihydro-2,2-dimethyl-4-(4-hydroxy-2-oxo-1-pyrrolidinyl)-2H-1-benzopyran-3-ol

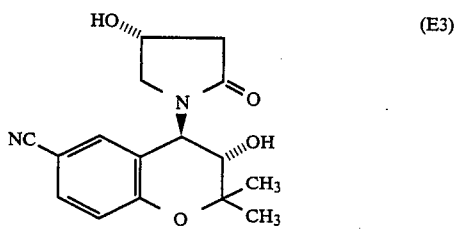
(E3)

A mixture of (+)-trans-4-amino-6-cyano-3,4-dihydro-2,2-dimethyl-2H-1-benzopyran-3-ol (5.2g) ($[\alpha]_D^{26}$ +82.9° (c,1.0, methanol)) and 3,4-epoxybutyric acid (10.5 g) in ethanol (85 ml) was stirred and refluxed for 24 hr. The solution was cooled and evaporated to dryness. The residue obtained crystallized on addition of ethyl acetate-diethyl ether. Filtration gave a white powder (3.54 g) which was chromatographed on silica gel using chloroform→15% methanol-chloroform in a gradient elution. Recrystallisation of the least polar diastereoisomer (ethyl acetate-ethanol) gave the (−)-4′-β-hydroxy compound (0.345 g), mp 265°–266° C.(d); $[\alpha]_D^{25}$ −34.7° (c,1.0, methanol).

Recrystallisation of the more polar diastereoisomer (ethyl acetate-ethanol) gave the (−)-4′-α-hydroxy compound (1.25g) (E3), mp 260°–261° C.; $[\alpha]_D^{25}$ −13.6° (c, 1.0, methanol).

PHARMACOLOGICAL DATA

Systolic blood pressures were recorded by a modification of the tail cuff method described by I. M. Claxton, M. G. Palfreyman, R. H. Poyser, R. L. Whiting, European Journal of Pharmacology, 37, 179 (1976). A W+W BP recorder, model 8005 was used to display pulses. Prior to all measurements rats were placed in a heated environment (33.5°±0.5° C.) before transfer to a restraining cage. Each determination of blood pressure was the mean of at least 6 readings. Spontaneously hypertensive rats (ages 12–18 weeks) with systolic blood pressures >180 mmHg were considered hypertensive.

| Compound of Example 2 (α-epimer) | Time Post Dose Hrs | % Change in Systolic Blood Pressure |
|---|---|---|
| 6 Rats | 1* | −49 ± 0 |
| Dose 10 mg/kg p.o. | 2** | −46 ± 5 |
| Initial Blood | 4** | −29 ± 6 |
| Pressure | 6** | −40 ± 5 |
| 264 ± 5 mmHg | 24 | −5 ± 3 |

*3 rats had no measurable pulse
**2 rats had no measurable pulse

We claim:

1. A compound of formula (I):

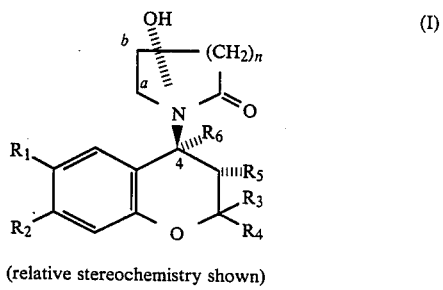
(I)

(relative stereochemistry shown)

wherein:
either one of $R_1$ and $R_2$ is hydrogen and the other is $C_{1-6}$ alkylcarbonyl, $C_{1-6}$ alkoxycarbonyl, nitro, cyano or trifluoromethyl, or one of $R_1$ and $R_2$ is nitro, cyano or $C_{1-3}$ alkylcarbonyl and the other is amino unsubstituted or substituted by one or two $C_{1-6}$ alkyl or by $C_{2-7}$ alkanoyl; one of $R_3$ and $R_4$ is hydrogen or $C_{1-4}$ alkyl and the other is $C_{1-4}$ alkyl or $R_3$ and $R_4$ together are $C_{2-5}$ polymethylene; either $R_5$ is hydrogen, hydroxy, $C_{1-6}$ alkoxy or $C_{1-7}$ alkanoloxy and $R_6$ is hydrogen or $R_5$ and $R_6$ together are a bond; and n is 1; and the hydroxy group substituting the lactam group is other than at the position a; and the substituted lactam group being trans to the $R_5$ group when $R_5$ is hydroxy, $C_{1-6}$ alkoxy of $C_{1-7}$ alkanoyloxy; or a pharmaceutically acceptable salt thereof.

2. A compound according to claim 1 wherein $R_1$ is nitro, cyano or $C_{1-3}$ alkylcarbonyl and $R_2$ is hydrogen.

3. A compound according to claim 1 wherein $R_3$ and $R_4$ are both methyl groups.

4. A compound according to claim 1 wherein $R_5$ is hydroxy and $R_6$ is hydrogen.

5. A compound according to claim 1 wherein the hydroxy substituent on the lactam ring is at position 3- or 4-relative to the lactam nitrogen atom, and n is 1.

6. A compound according to claim 1 which is selected from the group consisting of
(±)-trans-6-cyano-3,4-dihydro-2,2-dimethyl-4-(3′-α-hydroxy-2-oxo-1-pyrrolidinyl)-2H-1-benzopyran-3-ol;
(±)-trans-6-cyano-3,4-dihydro-2,2-dimethyl-4-(4′α-hydroxy-2-oxo-1-pyrrolidinyl)-2H-1-benzopyran-3-ol, or the single (−)-isomer thereof.

7. A compound according to claim 1 in pharmaceutically acceptable form.

8. An antihypertensive pharmaceutical composition comprising an antihypertensive effective amount of a compound according to claim 1, and a pharmaceutically acceptable carrier.

9. A method of treatment of hypertension in mammals, which comprises the administration of an antihypertensive effective amount of a compound according to claim 1.

* * * * *

UNITED STATES PATENT AND TRADEMARK OFFICE
CERTIFICATE OF CORRECTION

PATENT NO. : 4,831,050

DATED : May 16, 1989

INVENTOR(S) : Frederick Cassidy; Erol A. Faruk

It is certified that error appears in the above-identified patent and that said Letters Patent is hereby corrected as shown below:

On the title page, please insert

--Foreign Application Priority Data

October 21, 1986 [GB]         United Kingdom......8625185--

Signed and Sealed this

Twentieth Day of March, 1990

Attest:

JEFFREY M. SAMUELS

*Attesting Officer*   *Acting Commissioner of Patents and Trademarks*